(12) United States Patent
Yang et al.

(10) Patent No.: US 12,121,626 B2
(45) Date of Patent: Oct. 22, 2024

(54) BLOOD COAGULATION-PROMOTING SILK FIBROIN-POLYPEPTIDE ELECTROSPUN MEMBRANE AND PREPARATION METHOD THEREOF

(71) Applicant: Zhejiang University, Zhejiang (CN)

(72) Inventors: Mingying Yang, Zhejiang (CN); Fang Lei, Zhejiang (CN); Yajun Shuai, Zhejiang (CN)

(73) Assignee: Zhejiang University, Hangzhou (CN)

( * ) Notice: Subject to any disclaimer, the term of this patent is extended or adjusted under 35 U.S.C. 154(b) by 505 days.

(21) Appl. No.: 17/542,473

(22) Filed: Dec. 5, 2021

(65) Prior Publication Data

US 2022/0088266 A1    Mar. 24, 2022

Related U.S. Application Data

(63) Continuation-in-part of application No. PCT/CN2020/098423, filed on Jun. 28, 2020.

(30) Foreign Application Priority Data

Jun. 28, 2019 (CN) .......................... 201910572186.0

(51) Int. Cl.
*A61K 38/10* (2006.01)
*A61L 24/00* (2006.01)
*A61L 24/10* (2006.01)

(52) U.S. Cl.
CPC ......... *A61L 24/108* (2013.01); *A61L 24/0015* (2013.01); *A61L 2300/252* (2013.01); *A61L 2300/418* (2013.01); *A61L 2400/04* (2013.01)

(58) Field of Classification Search
None
See application file for complete search history.

(56) References Cited

FOREIGN PATENT DOCUMENTS

CN      104114198 A    10/2014
CN      107137757 A    9/2017

OTHER PUBLICATIONS

Farokhi, Mehdi et al, "Overview of silk fibroin use in wound dressings." Trends Biotechnol. (2018) 36(9) p. 907-922.*
International search report of PCT Patent Application No. PCT/CN2020/098423 issued on Sep. 1, 2020.

* cited by examiner

*Primary Examiner* — Fred H Reynolds

(57) ABSTRACT

The present invention discloses a blood coagulation-promoting silk fibroin-polypeptide electrospun membrane and a preparation method thereof. The electrospun membrane is made by using silkworm silk fibroin as a carrier and adding the polypeptide GPRPPSEHLQIT. It is mainly used for promoting blood coagulation, and is a blood coagulation material that can targetedly bind to human fibrinogen. The preparation method includes the steps of dissolving, filtering, dialyzing, concentrating and freeze-drying silkworm cocoons after degumming to obtain silk fibroin freeze-dried powder. The polypeptide used in the present invention is a polypeptide obtained by self-screening. Compared with other polypeptides, it can specifically targetedly bind to human fibrinogen.

6 Claims, 2 Drawing Sheets

Specification includes a Sequence Listing.

BLOOD COAGULATION-PROMOTING SILK FIBROIN-POLYPEPTIDE ELECTROSPUN MEMBRANE AND PREPARATION METHOD THEREOF

CROSS-REFERENCE TO RELATED APPLICATION

The present application is a Continuation-in-part Application of PCT Application No. PCT/CN2020/098423 filed on Jun. 28, 2020, which claims the benefit of Chinese Patent Application No. 201910572186.0 filed on Jun. 28, 2019. The contents of the above are hereby incorporated by reference in their entirety.

REFERENCE TO SEQUENCE LISTING

A sequence listing is submitted as an ASCII formatted text filed via EFS-Web, with a file name of "Sequence_listing.TXT", a creation date of Dec. 3, 2021, and a size of 567 bytes. The sequence Listing filed via EFS-Web is part of the specification and is incorporated in its entirety by reference herein.

FIELD OF THE INVENTION

The present invention relates to the field of a blood coagulation material, and in particular, to a blood coagulation-promoting silk fibroin-polypeptide electrospun membrane and a preparation method thereof.

BACKGROUND OF THE INVENTION

The research and application of blood coagulation materials has always been an important field of medical research. Whether it is traumatic bleeding caused by daily life, a clinical operation or even a war and so on, the application of a procoagulant material is of great significance for rapid hemostasis, lifesaving, etc. Furthermore, the essence of blood coagulation is a process in which fibrinogen in blood turns into fibrin. Fibrinogen, as a blood coagulation factor I, plays a huge role in the blood coagulation function. Therefore, the blood coagulation material with the ability to targetedly bind to fibrinogen can highly enrich human fibrinogen, which is conducive to the formation of a fibrin net structure at the traumatic site and further promotion of blood coagulation.

Bombyx mori silk fibroin, as the natural polymer protein, has the advantages of excellent biocompatibility, degradability, easy processing and molding, and good mechanical properties, etc. It is often processed into a membrane, a gel, a stent and other materials for use in regenerative medicine and other fields. A polypeptide GPRPPSEHLQIT (SED ID NO: 1) can targetedly bind to human fibrinogen, and its addition to the blood coagulation material can enrich the human fibrinogen on the surface of the material, thereby promoting blood coagulation. Relative to a material that displays this sequence such as bacteriophages and other materials, the polypeptide has a higher purity and can enrich human fibrinogen on the surface of the material to a greater extent. Moreover, the polypeptide has better safety and biocompatibility, making it more suitable for use in a biomaterial. An electrospun membrane prepared by electrospinning technology has a nanofiber structure, and has a larger specific surface area and greater porosity, of which structural features are similar to those of many natural tissues and organs. The electrospun membrane made of silk fibroin is often used as a biomaterial. The rough surface structure of the silk fibroin electrospun membrane has better adhesion to protein under the blood flow state than that of other blood coagulation materials with a smooth surface, which is conducive to the formation of thrombus in the wound, the promotion of blood coagulation, and wound healing. However, the traditional silk fibroin electrospun membrane can only adhere to protein through the effects of electrostatic adsorption and other effects on the surface, and cannot targetedly bind to protein. Human fibrinogen serves as protein that can significantly affect the blood coagulation ability. In order to targetedly bind to human fibrinogen on the surface of the material, we added the polypeptide GPRPPSEHLQIT (SED ID NO: 1) that can targetedly bind to human fibrinogen to make a silk fibroin-polypeptide electrospun membrane. The electrospun membrane can targetedly bind to human fibrinogen in the blood on the surface, which is conducive to the formation of a fibrin net structure on the surface of the material and the promotion of wound blood coagulation.

SUMMARY OF THE INVENTION

Aiming at the shortcomings in the field of traditional blood coagulation material, the present invention provides a silk fibroin-polypeptide electrospun membrane capable of targetedly binding to human fibrinogen and preparation method thereof. The present invention is an electrospun membrane made by using silkworm silk fibroin as a carrier and adding the polypeptide GPRPPSEHLQIT (SED ID NO: 1), which has a better blood coagulation effect than those of traditional blood coagulation materials and the pure silk fibroin electrospun membrane. The silk fibroin-polypeptide electrospun membrane prepared by the present invention is mainly used for promoting blood coagulation, and is a blood coagulation material that can targetedly bind to human fibrinogen. The specific technical solution of the present invention is as follows:

The present invention discloses a blood coagulation-promoting silk fibroin-polypeptide electrospun membrane, in which a sequence of the polypeptide used is GPRPPSEHLQIT (SED ID NO: 1), and a polypeptide concentration is 0.2 mg/mL-10 mg/mL.

As a further improvement, the electrospun membrane of the present invention is made of interwoven silk fibroin nanofibers, and the polypeptide is evenly distributed in the nanofibers.

The present invention further discloses a preparation method of the blood coagulation-promoting silk fibroin-polypeptide electrospun membrane, and the specific preparation steps adopted are as follows:

1) dissolving, filtering, dialyzing, concentrating, freeze-drying silkworm cocoons after degumming to obtain silk fibroin freeze-dried powder;

2) evenly mixing the silk fibroin freeze-dried powder and the polypeptide GPRPPSEHLQIT (SED ID NO: 1) with a hexafluoroisopropanol solvent;

3) electrospinning the mixed solution obtained in step 2) to obtain a silk fibroin-polypeptide electro spun membrane.

As a further improvement, the mass ratio of the silk fibroin freeze-dried powder to the hexafluoroisopropanol solvent used in step 2) of the present invention is 2:98-20:80.

As a further improvement, the concentration of the polypeptide GPRPPSEHLQIT (SED ID NO: 1) added in step 2) of the present invention is 0.2 mg/mL-10 mg/mL.

As a further improvement, the silk fibroin-polypeptide electro spun membrane prepared in step 3) of the present invention is subjected to alcohols treatment to obtain a water-insoluble silk fibroin-polypeptide electrospun membrane.

Compared with the prior art, the present invention has the following outstanding features.

(1) The polypeptide used in the present invention is a polypeptide obtained by self-screening. Compared with other polypeptides, it can specifically targetedly bind to human fibrinogen. The polypeptide is conducive to the formation of a fibrin net structure on the surface of the membrane and the promotion of blood coagulation by enriching human fibrinogen on the electrospun membrane.

(2) The polypeptide used in the electrospun membrane has higher biological safety than that of bacteriophages expressing this polypeptide sequence.

(3) The silk fibroin used in the electrospun membrane is a natural polymer protein. It has better biocompatibility and higher safety than those of other inorganic materials or synthetic polymer materials, and is convenient to manufacture, which facilitates mass production.

DETAILED DESCRIPTION OF THE EMBODIMENTS

The technical solution of the present invention will be explained in details with reference to the specific examples. The following examples are for explaining the present invention and the present invention is not limited to the following examples.

EXAMPLE 1

(1) 60 g of silkworm cocoons were weighed, and were mixed with 6 L of 5 g/L $NaCO_3$. After the boiling for 30 minutes, the silk was rinsed thoroughly with deionized water. The above mixing, boiling and rinsing procedure was repeated once followed by drying to obtain silk fibers.

(2) 10 g of the silk fibers were taken and were mixed with 100 mL of 9.3 M LiBr. The mixture was subjected to a 60° C. water bath for 4 h followed by filtration with gauze. After the dialysis in a dialysis bag for 3 days, concentration was performed to obtain a silk fibroin solution.

(3) The silk fibroin solution was freeze-dried to obtain silk fibroin freeze-dried powder. 2 g of the silk fibroin freeze-dried powder was weighed, and was evenly mixed with 8 g of a hexafluoroisopropanol solvent. 1 mL of this mixed solution was then taken and 10 mg of polypeptide GPRPPSEHLQIT (SED ID NO: 1) was added thereto to obtain an electrospinning solution.

Figure 1:
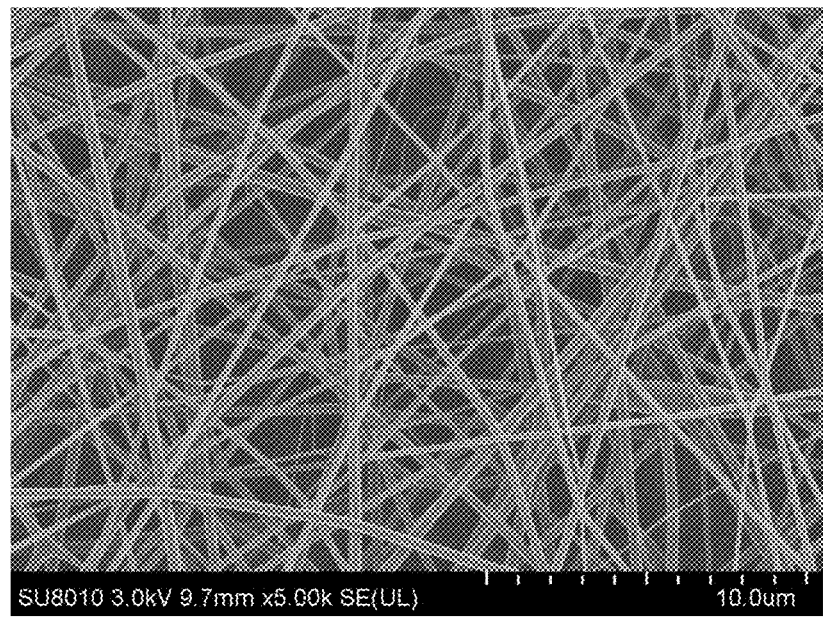
FIG. 1 is an electron micrograph of a silk fibroin-polypeptide electrospun membrane.

(4) The electrospinning solution obtained in step 3) was electrospun at a speed of 0.2 mL/min to obtain a silk fibroin-polypeptide electrospun membrane. The electrospun membrane was observed with a scanning electron microscope to obtain FIG. 1.

EXAMPLE 2

(1) 20 g of silkworm cocoons were weighed, and were mixed with 1 L of 5 g/L $NaCO_3$. After the boiling for 30 minutes, the silk was rinsed thoroughly with deionized water. The above mixing, boiling and rinsing procedure was repeated once followed by drying to obtain silk fibers.

(2) 10 g of the silk fibers were taken, and were mixed with 30 mL of 9.3 M LiBr. The mixture was subjected to a 60° C. water bath for 2 h followed by filtration with gauze. After the dialysis in a dialysis bag for 3 days, concentration was performed to obtain a silk fibroin solution. The silk fibroin solution was then freeze-dried to obtain silk fibroin freeze-dried powder.

(3) 1 g of the silk fibroin freeze-dried powder was mixed with 13.29 g of a hexafluoroisopropanol solvent. 1 mL of this mixed solution was taken respectively, and 0, 0.2, 0.4, 0.6 and 1 mg of polypeptide GPRPPSEHLQIT (SED ID NO: 1) were added thereto respectively to obtain solutions to be obtained in step 3).

(4) The solutions obtained in step 3) were electrospun respectively to obtain silk fibroin-polypeptide electrospun membranes.

Figure 2:
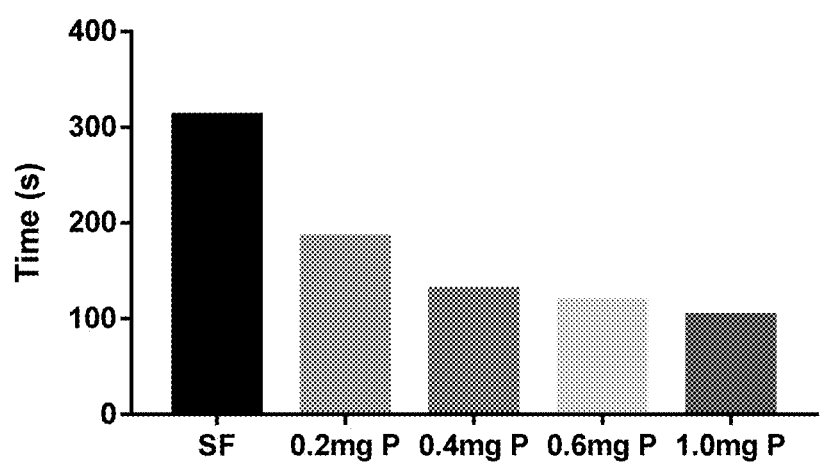
FIG. 2 is a graph showing the results of the activated partial thromboplastin time (APTT) of silk fibroin-polypeptide electrospun membranes with the addition of polypeptides (P) of different masses and pure silk fibroin electrospun membrane.

(5) These electrospun membranes were detected for the activated partial thromboplastin time (APTT), and the results shown in FIG. 2 can be obtained, indicating that as the polypeptide concentration goes up, the required time will become short, and representing that the higher the polypeptide concentration is, the better the blood coagulation effect is.

EXAMPLE 3

(1) 20 g of silkworm cocoons were weighed, and were mixed with 2 L of 5 g/L $NaCO_3$. After the boiling for 30 minutes, the silk was rinsed thoroughly with deionized water. The above mixing, boiling and rinsing procedure was repeated once followed by drying to obtain silk fibers.

(2) 10 g of the silk fibers were taken, and were mixed with 100 mL of 9.3 M LiBr. The mixture was subjected to a 60°

C. water bath for 4 h followed by filtration with gauze. After the dialysis in a dialysis bag for 3 days, concentration was performed to obtain a silk fibroin solution. The silk fibroin solution was then freeze-dried to obtain silk fibroin freeze-dried powder.

(3) 0.2 g of the silk fibroin freeze-dried powder was mixed with 9.8 g of a hexafluoroisopropanol solvent. 1 mL of this mixed solution was taken respectively, and 0.2 mg of polypeptide GPRPPSEHLQIT (SED ID NO: 1) was added thereto. Another 1 mL of this mixed solution was taken, and 0.2 mg of other polypeptide was added thereto for control. Solutions to be obtained in step 3) were obtained.

(4) The solutions obtained in step 3) were electrospun respectively to obtain silk fibroin-polypeptide electrospun membranes.

Figure 3:
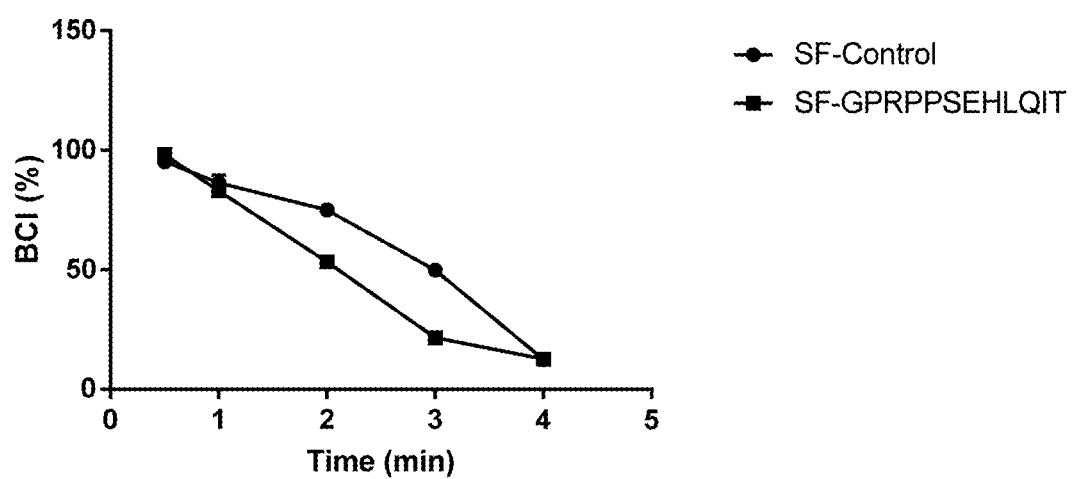
FIG. 3 is a graph showing the results of Blood Coagulation Index (BCI) of electrospun membranes with the addition of the polypeptide GPRPPSEHLQIT (SED ID NO: 1) and polypeptides of different sequences.

(5) The above electrospun membranes were mixed with fresh blood followed by incubation at 37° C. for 0.5, 1, 2, 3 and 4 min respectively. After blood clots were removed, the content of hemoglobin in the uncoagulated blood was detected, of which the ratio in the total hemoglobin content before blood coagulation is the Blood Coagulation Index (BCI). FIG. 3 can be obtained. The faster the index decreased, the faster the blood coagulation speed was, indicating that the electrospun membrane with the addition of the polypeptide GPRPPSEHLQIT (SED ID NO: 1) has a better blood coagulation-promoting effect than that of the electrospun membrane with the addition of other polypeptide.

EXAMPLE 4

(1) 60 g of silkworm cocoons were weighed, and were mixed with 6 L of 5 g/L NaCO$_3$. After the boiling for 30 minutes, the silk was rinsed thoroughly with deionized water. The above mixing, boiling and rinsing procedure was repeated once followed by drying to obtain silk fibers.

(2) 10 g of the silk fibers were taken, and were mixed with 100 mL of 9.3 M LiBr. The mixture was subjected to a 60° C. water bath for 2 h followed by filtration with gauze. After the dialysis in a dialysis bag for 3 days, concentration was performed to obtain a silk fibroin solution. The silk fibroin solution was then freeze-dried to obtain silk fibroin freeze-dried powder.

(3) 1 g of the silk fibroin freeze-dried powder was mixed with 9 g of a hexafluoroisopropanol solvent. 1 mL of this mixed solution was taken and 5 mg of a polypeptide GPRPPSEHLQIT (SED ID NO: 1) was added thereto to obtain a solution to be obtained in step 3).

(4) The solution obtained in step 3) was electrospun to obtain a silk fibroin-polypeptide electrospun membrane.

(5) The silk fibroin-polypeptide electrospun membrane was soaked in 90% ethanol for 30 min to obtain a water-insoluble silk fibroin-polypeptide electrospun membrane.

Finally, it should be noted that the above-listed are only specific examples of the present invention. Obviously, the present invention is not limited to the above examples, and many variations are possible. All variations that can be directly derived or imagined by those skilled in the art from the disclosure of the present invention shall be regarded as the protection scope of the present invention.

The invention claimed is:

1. A blood coagulation-promoting silk fibroin-polypeptide electrospun membrane, wherein the polypeptide has a sequence of GPRPPSEHLQIT (SED ID NO: 1).

2. The silk fibroin-polypeptide electrospun membrane according to claim 1, wherein the electrospun membrane is made of interwoven silk fibroin nanofibers, and the polypeptide is evenly distributed in the nanofibers.

3. A preparation method of the blood coagulation-promoting silk fibroin-polypeptide electrospun membrane according to claim 1, wherein specific preparation steps adopted are as follows:
1) dissolving, filtering, dialyzing, concentrating, freeze-drying silkworm cocoons after degumming to obtain silk fibroin freeze-dried powder;
2) evenly mixing the silk fibroin freeze-dried powder and the polypeptide GPRPPSEHLQIT (SED ID NO: 1) with a hexafluoroisopropanol solvent;
3) electrospinning a mixed solution obtained in step 2) to obtain a silk fibroin-polypeptide electrospun membrane.

4. The preparation method of the silk fibroin-polypeptide electrospun membrane according to claim 3, wherein the mass ratio of the silk fibroin freeze-dried powder: the hexafluoroisopropanol solvent used in the step 2) is 2:98-20:80.

5. The preparation method of the silk fibroin-polypeptide electrospun membrane according to claim 3, wherein a concentration of the polypeptide GPRPPSEHLQIT (SED ID NO:1) added in the step 2) is 0.2 mg/mL-10 mg/mL.

6. The preparation method of the silk fibroin-polypeptide electrospun membrane according to claim 3, wherein, the silk fibroin-polypeptide electrospun membrane prepared in step 3) is subjected to alcohol treatment to obtain a water-insoluble silk fibroin-polypeptide electrospun membrane.

* * * * *

```
SEQUENCE LISTING

<160> NUMBER OF SEQ ID NOS: 1

<210> SEQ ID NO 1
<211> LENGTH: 12
<212> TYPE: PRT
<213> ORGANISM: Artificial Sequence
<220> FEATURE:
<223> OTHER INFORMATION: Synthetic

<400> SEQUENCE: 1

Gly Pro Arg Pro Pro Ser Glu His Leu Gln Ile Thr
1               5                   10
```